United States Patent [19]
Kury et al.

[11] Patent Number: 5,958,299
[45] Date of Patent: Sep. 28, 1999

[54] EXPLOSIVE SIMULANTS FOR TESTING EXPLOSIVE DETECTION SYSTEMS

[75] Inventors: John W. Kury, Danville; Brian L. Anderson, Lodi, both of Calif.

[73] Assignee: Regents of the University of California, Oakland, Calif.

[21] Appl. No.: 08/980,613

[22] Filed: Dec. 1, 1997

[51] Int. Cl.⁶ .......................... G01N 31/00; G01N 33/00
[52] U.S. Cl. .................... 252/408.1; 102/355; 149/89
[58] Field of Search .................. 252/408.1; 102/355; 149/89

[56] References Cited

U.S. PATENT DOCUMENTS

| | | |
|---|---|---|
| 3,457,329 | 7/1969 | Silver et al. . |
| 5,182,764 | 1/1993 | Peschmann et al. ............. 378/57 |
| 5,319,547 | 6/1994 | Krug et al. ..................... 364/409 |
| 5,359,936 | 11/1994 | Simpson et al. ................ 102/355 |
| 5,413,812 | 5/1995 | Simpson et al. ................ 427/212 |
| 5,648,636 | 7/1997 | Simpson et al. ................ 102/355 |
| 5,756,006 | 5/1998 | Reed, Jr. et al. .............. 252/408.1 |

OTHER PUBLICATIONS

Eilbert, R.F., 1996; Development and Evaluation of Simulants for X–ray Based Explosive Detection Systems, in Second FAA/AAAE Explosives Detection Symposium and Aviation Security Technology Conf., Nov. 12–15, 1996, Atlantic City, NJ.

Kropas, C.V., T.J. Moran, and R.N. Yancey, 1990; Effect of Composition on Density Measurement by X–ray Computed Tomography in Materials Evaluation, Apr. 1991, pp. 487–490.

*Primary Examiner*—Krisanne Thornton
*Attorney, Agent, or Firm*—Daryl S. Grzybicki

[57] ABSTRACT

Explosives simulants that include non-explosive components are disclosed that facilitate testing of equipment designed to remotely detect explosives. The simulants are non-explosive, non-hazardous materials that can be safely handled without any significant precautions. The simulants imitate real explosives in terms of mass density, effective atomic number, x-ray transmission properties, and physical form, including moldable plastics and emulsions/gels.

17 Claims, No Drawings

EXPLOSIVE SIMULANTS FOR TESTING EXPLOSIVE DETECTION SYSTEMS

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to the composition of non-explosive, non-hazardous explosive simulants that can be used to test equipment designed to remotely detect explosives.

2. Description of Related Art

The Federal Aviation Administration (FAA) has used explosive simulants for many years to field test various automated explosive detection systems embedded within baggage inspection systems at airports, and to train the operators of this equipment. The FAA develops and validates training aids for baggage inspectors and hand-searchers to help them distinguish threats from false alarms. The best explosive simuiant is a physical model that imitates selected attributes of the more complex, real-world system. Simulators are particularly useful to hone, test, and evaluate the abilities of personnel and equipment when a real-world environment is too costly or not available.

The FAA and Lawrence Livermore National Laboratory have previously collaborated on a type of explosive simulant for canine-trace detection and training, referred to as Non-Energetic Simulants for Training and Testing (NESTT). NESTT materials use a trace quantity of explosive material diluted in various inert substances. Although explosive material is present, the NESTT materials are not detonable or explosive. See U.S. Pat. Nos. 5,359,936, 5,413,812, and 5,648,636 to Simpson et al.

The need for better explosive simulants becomes more critical as the threat to airport security increases and the ability of equipment to discern secondary bulk explosives improves. Existing simulants have significant limitations that prevent their valid use in field testing many of the recently developed explosive detection systems. For example, the NESTT materials, although non-detonable, still require handling of actual explosive material. Also, many of the conventional simulants simply do not fool the automated explosive detection systems; if they do, the simulants frequently cause the systems to report misleading information that can either confuse an operator or compromise a detection performance test, or both. The conventional use of rigid plastics has limited the physical form and concealment types in improvised explosive device design, and represents a fairly narrow coverage of explosive types. This limitation in particular has made the development of simulants of more pliable explosive materials, as well as explosive emulsions and gels, quite desirable.

Because the conventional simulants have limited usefulness in training operators, testing automated x-ray detection systems, and accurately simulating improvised explosive devices, there is a need for explosive simulants that contain no trace explosive materials, yet exhibit accurately controlled physical properties that specifically and reliably duplicate selected characteristics of real explosives which are recognized by specific explosive detection systems. The present invention addresses these challenges.

SUMMARY OF THE INVENTION

The present invention is a group of explosive simulant materials that are designed to imitate the physical form, homogeneity, x-ray transmission properties, mass density, and effective atomic number ($Z_{eff}$) of real explosives, without containing any of the explosive material being simulated. The explosive simulants exhibit chemical stability and provide a relatively large margin of safety compared to explosives. The simulants are comprised of low Z, high density components that produce the desired mass density and effective atomic number, which corresponds to an x-ray transmission profile that matches the simulated explosive.

In general, the present invention focuses on simulating secondary high explosives used in military and commercial applications, such as C-4, SEMTEX, Detasheet, TNT (trinitrotoluene), nitroglycerin (NG) dynamite, and ANFO (ammonium nitrate fuel oil) emulsions and gels, as well as low velocity commercial explosives (e.g., black and smokeless powders). These explosives include a large variety of nitrated organics (i.e., carbon skeletons) doped with various additives as appropriate.

Substituting completely inert simulants for explosives offers significant benefits in testing explosive detection systems and in training operators. These simulants greatly improve safety and handling simplicity, and offer a larger representation of explosive-type diversity beyond the constraints imposed by that available in existing local explosives storage magazines. They also open up previously prohibited domains permitting their use in forms and locations in articles which, as explosives, would otherwise be hazardous or irreversible. Matching the physical properties of the simulant to the corresponding real explosive is important so that the simulant can be concealed and handled in the same manner as would the real explosive.

DETAILED DESCRIPTION OF THE INVENTION

The present invention is a class of explosive simulant materials that do not contain any of the explosive material being simulated. These materials are designed to possess certain characteristics that mimic selected explosive materials. Specifically, these characteristics include matched physical form and homogeneity, matched x-ray transmission properties, matched mass density, and matched effective atomic number ($Z_{eff}$). In addition, the explosive simulants exhibit chemical stability and are designed to provide a relatively large margin of safety compared to explosives. The x-ray transmission profile is measured by Computed Tomography (CT) and can be expressed as CT-density, which is a critical feature for testing certain commercially available explosive detection systems (e.g., InVision CTX 5000SP®). Other commercial systems (e.g., Vivid FS®) use algorithms that key on the effective atomic number ($Z_{eff}$) of the object.

The simulants are physical mixtures of two or more non-explosive components, such as those listed in the examples given in Table I. None of the components are regulated materials under DOT 49 CFR Part 172, which governs transportation of hazardous materials. The components have minimal acute toxicity hazard levels or none at all according to published hazard and probable lethal dose assessment tables.

The explosives that are simulated have various physical forms, including solids and powders (e.g., military explosives, aluminized explosives, trinitrotoluene (TNT), black powder, smokeless powder, blasting agent ANFO), moldable (putty-like) or flexible (rubber-like) plastics (e.g., C-4, SEMTEX, a plastic explosive containing cyclotrimethylene-trinitramine and pentaerythritoltetranitrate Detasheet, XTX 8003), and emulsions or gels (e.g., ammonium nitrate and nitroglycerin blasting gelatins). The explosive simulants are designed to closely mimic the physical form of the simulated explosive. These different physical forms permit more accurate representation of real-world explosives and more realistic concealment of improvised explosive devices in test bags.

For solid form simulants, the non-explosive components are in powder form and are simply mixed together. The homogeneous powder may be pressed to increase (or maximize) its density. The powder may be pressed into a plastic sheet using rollers (e.g., Detasheet simulant). To achieve maximum density, the grain size of the components may be controlled, but is typically in the range of about 50–150 microns.

In the case of plastic simulants, the plastic (polymeric) components are typically mixed with a solvent, and any solid (inorganic) powders are mixed separately. The polymer solution and powders are blended together, and the solvent is evaporated, either under ambient temperature and pressure, or under vacuum to speed the process. The solvent is a volatile organic that can easily dissolve the polymeric components and then be removed (evaporated) from the mixture. Typical low boiling point organic solvents include ketones (acetone, methylethyl ketone), ethers, alcohols, and alkynes (pentane, octane). A non-volatile industrial oil (e.g., SAE 40) may be included as a simulant component to act as a binder to produce the desired pliable (moldable) plastic form having clay-like or rubber-like consistency. The solid plastic forms can be cut into desired shapes.

For emulsion/gel simulants, the final material is formed of water, a gelling agent (or agents) and solid powders mixed together. More specifically, an emulsion/gel simulant may be formed by mixing the solids in a solution of water with a first gelling agent (e.g., Carbopol™) to achieve a homogeneous viscous mixture, and then adding a second gelling agent (e.g., triethanolamine, which acts with Carbopol™) to form the final gel. The gelling may occur in a matter of minutes, or hours, depending on the choice of gelling agent(s).

In general, the choice and proportion of components is determined by the physical form desired and the mass density and effective atomic number needed to simulate the x-ray transmission profile (CT-density) of the simulated explosive. Examples of components and binders for making simulants include boron carbide, carbon, aluminum, industrial oil (e.g., SAE 40), organic wax (e.g., TONE 260™), cyanuric acid, dioctyl adipate, estane, ethylene vinyl acetate, polyisobutylene, polyethylene, gelled water, and metal oxides, such as silica, ferric oxide, and alumina. This list is by no means exhaustive; any organic or inorganic components that can achieve the desired mass density and effective atomic number could be used, although nitrates are avoided. In some cases, a non-explosive component of a real explosive (e.g., oil) is also used in the simulant to help mimic the properties of the explosive.

The simulant explosives of the present invention are designed to match the attribute of the explosive's x-ray transmission profile as measured by CT-density, since certain commercially available explosive detection systems have automated alarms that are triggered primarily by the object's CT-density. CT-density is typically reported on an explosive detection system (EDS) using a linear CT-number scale. For example, the InVision CTX 5000SP® EDS defines air as having a CT-number as 0 and water as 1000. Excluding atomic number effects, the CT-number can be roughly calculated as the mass density (pm)×1000.

In general, x-ray computed tomography is a non-destructive, radiographic method that provides a quantitative densitometric image based on a thin slice through an object. The cross-sectional image generated by this slice is a CT-density map derived from an averaged value of the linear attenuation coefficient ($\mu_L$) in each pixel. These coefficients are the local, instantaneous rates at which x-ray photons are absorbed or scattered from the x-ray tube per unit of distance traveled in the object.

Each attenuation coefficient is the sum of the attenuation (or photon interaction) processes that occurred in that volume element (predominantly Compton or inelastic scattering and/or photoelectric interaction), which are in turn dependent upon the energy of the x-ray photon and the elemental composition (atomic number) of the object. Photoelectric interaction occurs when an x-ray photon bumps out a tightly bound electron, and is strongly dependent on the atomic number and $\rho_M$ of the absorbing medium. Compton scattering occurs when an x-ray photon releases a loosely bound electron and is predominantly dependent on $\rho_M$. In Compton scattering, $\mu L$ is proportional to the object's electron-density ($\rho_e$), which is calculated as $\rho_M$ times a near-constant ratio value (approximately $3.0 \times 10^{23}$ electrons/gram), and which is only slightly sensitive and inversely proportional to atomic number.

In general, $\mu_L$ is calculated using Lambert's law of absorption where the line integral $$\int \mu_L(s)ds = -ln(I/I_o)$$

is computed at each point on the ray path along the direction of propagation and subsequently adjusted to account for a polychromatic source. $I_o$ is the intensity of the incident radiation, and I is the intensity of the transmitted flux after penetrating a non-homogeneous material. Thus, CT-density is related to the line integral of the linear absorption coefficient, which is in turn dependent upon the x-ray photon energy, and the mass density ($\rho_M$) and effective atomic number (though weakly) of the absorbing material.

The simulant explosives of the present invention are also designed to match the attribute of the explosive's effective Z number, since other commercially available explosive detection systems (e.g., Vivid FS®) have automated alarm algorithms that depend primarily on the $Z_{eff}$ of the object. Consequently, for the simulants to be valid for testing this equipment, they must match the effective atomic number of the real explosives. Two approaches are used to match and validate simulants for this use: an analytical model using a weighted elemental analysis of the chemical formula, and a direct $Z_{eff}$ measurement using Vivid's analytical tool called center-alpha. Acceptable match accuracy was defined to be within ±2.5% of the targeted effective atomic number of each explosive type. The range of $Z_{eff}$ for simulant explosives is about 6–15.

In general, the analytical model assumes that the simulant materials consist of a mixture of elements or compounds. A uniform simulant material will attenuate x-rays as if it were composed of a single effective atomic number, $Z_{eff}$, which in general is a non-integer value. $Z_{eff}$ depends solely on the elemental composition and is essentially independent of x-ray energy. Assuming a uniform compound consisting of N elements, having an atomic number $Z_i$ and contributing mass $m_i$, the average atomic number is $$Z_{ave} = \Sigma(m_i)(Z_i)/\Sigma m_i.$$

The average atomic number can differ substantially from $Z_{eff}$, which more strongly weights the higher Z elements in the compound. The formula for $Z_{eff}$ is given by $Z_{eff}=(\Sigma(a_i)(Z_i)^{3.5}/\Sigma(a_i))^{1/3.5}$, where $a_i=(m_i)(Z_i)/A_i$, and $A_i$ is the atomic weight. (For further description of how $Z_{eff}$ is calculated, refer to Eilbert, R. F., Development and Evaluation of Simulants For X-ray based Explosive Detection Systems, Second FAA/AAAE Explosives Detection Symposium and Aviation Security Technology Conference, Nov. 12–15, 1996, Atlantic City, N.J.)

Explosive simulants can be designed, therefore, by carefully selecting the composition and amount of the material components (reagents), their measured mass densities, their grain sizes (if appropriate), and the theoretical effective atomic number of the final composition. Using these considerations, explosive simulants were created that mimic the physical form, mass density and effective atomic number of all types of explosives (powders, plastics, and emulsions/gels). Examples of explosive simulants are provided in Table I.

An imaging tool was used to measure the CT-density of the simulants in slices taken by the InVision CTX 5000SP®. The mass density of the simulants was also measured, and air accounted for the difference between theoretical mass densities of the physical mixes and volumetric tap-density measurements. For powders, the physical packing of multi-sized grains presented an interesting variance in the effective tap-density. Acceptable match accuracy was defined to be within ±10% of targeted mass density or roughly ±0.1 grams/cm$^3$ (or about 100 CT#). For powders, the choice of grain size was matched to that of dominant explosive class representatives. In emulsions/gels, the number and size of air bubbles and the gelling stiffness can be controlled by process modifications and the amount of gelling agent.

The homogeneity of the simulant and real explosive can be quantitatively compared using the radiographic texture of the material as revealed by the gray-scale intensities used in the slice image. The intensity variance among pixels is linearly related to homogeneity of the material, and was measured using an imaging tool on the InVision CTX 5000SP®. The intensity variance of the simulant was within 25% of the intensity variance of the real explosive. The Vivid equipment can be used to measure the simulant's effective atomic number, which was found to be within 5% of the target (explosive).

TABLE I

Simulant Compositions

| Simulated Material | Composition (wt %) | Physical form | Density (g/cc) |
| --- | --- | --- | --- |
| TNT | 11% estane<br>80% cyanuric acid<br>8% polyethylene<br>1% silica | solid | 1.4 |
| SEMTEX | 12% dioctyl adipate<br>4% oil<br>4% polyisobutylene<br>55% cyanuric acid<br>19% boron carbide<br>6% silica | plastic | 1.5 |
| Smokeless powder | 30% cyanuric acid<br>57% polyethylene<br>13% silica | powder | 0.7 |
| High density commercial high explosive | 26% boron carbide<br>51% gelled water<br>8% polyethylene<br>16% silica | emulsion/gel | 1.3 |

The foregoing description of preferred embodiments of the invention is presented for purposes of illustration and description and is not intended to be exhaustive or to limit the invention to the precise form disclosed. Many modifications and variations are possible in light of the above teaching.

We claim:

1. An explosive simulant for testing explosive detection systems, comprising:

a non-detonable, non-explosive mixture of a plurality of non-explosive compounds having no explosive compounds, wherein the components are selected such that the mixture has a physical form, mass density, x-ray transmission properties, and an effective atomic number that substantially matches the physical form, mass density, x-ray transmission properties, and effective atomic number of a selected explosive compound to be simulated.

2. The explosive simulant as recited in claim 1, wherein the mixture includes at least two solid powder compounds, and the simulant is a homogeneous, packed powder mixture.

3. The explosive simulant as recited in claim 1, wherein the mixture includes at least one polymeric or plastic compound and at least one inorganic solid compound, and the simulant is a moldable plastic material.

4. The explosive simulant as recited in claim 3, wherein the mixture further comprises an oil compound.

5. The explosive simulant as recited in claim 1, wherein the mixture includes at least one polymeric or plastic compound and at least one inorganic solid compound, and the simulant is a solid material.

6. The explosive simulant as recited in claim 1, wherein the mixture includes at least one solid powder compound, water, and at least one gelling agent, and the simulant is gel or emulsion.

7. The explosive simulant as recited in claim 6, wherein the mixture further includes at least one polymeric compound.

8. The explosive simulant as recited in claim 1, wherein at least one of the non-explosive compounds is selected from the group consisting of boron carbide, carbon, aluminum, industrial oil, organic wax, cyanuric acid, dioctyl adipate, estane, ethylene vinyl acetate, polyisobutylene, polyethylene, gelled water, and metal oxides.

9. The explosive simulant as recited in claim 1, wherein the physical form of the simulant and the selected explosive compound is selected from solids, powders, moldable plastics, flexible plastics, emulsions, and gels.

10. The explosive simulant as recited in claim 1, wherein the explosive compound is selected from the group consisting of aluminized explosives, trinitrotoluene, black powder, smokeless powder, ammonium nitrate fuel oil, plastic explosives, Detasheet, nitroglycerin dynamite, and ammonium nitrate and nitroglycerin blasting gelatins.

11. The explosive simulant as recited in claim 1, wherein the x-ray transmission properties are measured as computed tomography (CT) density.

12. A process for making an explosive simulant, comprising:

forming a non-detonable, non-explosive mixture of a plurality of non-explosive compounds having no explosive compounds, wherein the components are selected such that the mixture has a physical form, mass density, x-ray transmission properties, and an effective atomic number that substantially matches the physical form, mass density, x-ray transmission properties, and effective atomic number of a selected explosive compound to be simulated.

13. The process as recited in claim 12, wherein the mixture includes at least two solid powder compounds, and wherein forming the mixture is carried out by mixing the powder compounds to form a homogeneous powder mixture.

14. The process as recited in claim 12, wherein the mixture includes at least one polymeric or plastic compound and at least one inorganic solid compound, and wherein forming the mixture is carried out by mixing the polymeric compound, in an organic solvent, adding the inorganic compound to form a homogeneous solution, and removing the solvent to form a plastic simulant.

15. The process as recited in claim 14, further comprising adding an oil compound to the solution.

16. The process as recited in claim 12, wherein the mixture includes at least one solid powder compound, water, and at least one gelling agent, and wherein forming the mixture is carried out by mixing the water and gelling agent, adding the solid compound to form a homogeneous solution, and gelling the solution to form a gel or emulsion simulant.

17. The process as recited in claim 16, wherein the mixture includes at least one polymeric compound, and wherein forming the mixture is further carried out by adding the polymeric compound with the solid compound.

* * * * *